US012746298B2

(12) United States Patent
Zhu et al.

(10) Patent No.: US 12,746,298 B2
(45) Date of Patent: Sep. 29, 2026

(54) DEVICE FOR SKIN DISINFECTION AND ADHESIVE DEACTIVATION

(71) Applicant: Becton, Dickinson and Company, Franklin Lakes, NJ (US)

(72) Inventors: Linjie Zhu, Livingston, NJ (US); Kevin M. Ryan, Whitehouse Station, NJ (US); Shishir Prasad, Ramsey, NJ (US); Angela Marie Huenerfauth, Morris Plains, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 271 days.

(21) Appl. No.: 18/688,371

(22) PCT Filed: Sep. 1, 2022

(86) PCT No.: PCT/US2022/042286
§ 371 (c)(1),
(2) Date: Mar. 1, 2024

(87) PCT Pub. No.: WO2023/034468
PCT Pub. Date: Mar. 9, 2023

(65) Prior Publication Data

US 2025/0001020 A1 Jan. 2, 2025

Related U.S. Application Data

(60) Provisional application No. 63/240,029, filed on Sep. 2, 2021.

(51) Int. Cl.

| | |
|---|---|
| ***A61N 5/00*** | (2006.01) |
| ***A61L 2/10*** | (2006.01) |
| *A61L 103/05* | (2026.01) |

(52) U.S. Cl.
CPC ............ *A61L 2/10* (2013.01); *A61L 2103/05* (2026.01)

(58) Field of Classification Search
CPC ................ A61N 5/0616; A61N 5/0624; A61N 2005/0061; A61N 2005/0662;
(Continued)

(56) References Cited

U.S. PATENT DOCUMENTS 4,999,242 A 3/1991 Ishiwata et al.
6,293,281 B1 * 9/2001 Shultz ................. A61B 17/085 602/43

(Continued)

FOREIGN PATENT DOCUMENTS

EP 2957611 A1 12/2015
WO 2017048877 A1 3/2017

(Continued)

*Primary Examiner* — Sana Sahand
(74) *Attorney, Agent, or Firm* — The Webb Law Firm

(57) ABSTRACT

A device including a housing, a disinfecting light source coupled to the housing, where the disinfecting light source is configured to disinfect an object, an adhesive light source coupled to the housing, where the adhesive light source is configured to cause a light switchable adhesive to transition between an adhering state and a removal state based on the light switchable adhesive being exposed to light emitted by the adhesive light source, and an activation sensor coupled to the housing, wherein the activation sensor is electrically coupled to the disinfecting light source and the adhesive light source, and wherein the activation sensor is configured to cause the disinfecting light source and the adhesive light source to activate.

26 Claims, 3 Drawing Sheets

(58) Field of Classification Search
CPC ...... A61L 2/0047; A61L 2/20; A61L 2202/11; A61L 2202/14; A61L 2202/24
See application file for complete search history.

(56) References Cited

U.S. PATENT DOCUMENTS

| | | | | |
|---|---|---|---|---|
| 8,043,699 | B2 | 10/2011 | Rosing et al. | |
| 8,697,932 | B2 | 4/2014 | Tunius | |
| 2012/0004628 | A1 | 1/2012 | Blott et al. | |
| 2018/0084956 | A1* | 3/2018 | Childress | A47K 10/48 |
| 2020/0151410 | A1* | 5/2020 | Wagner | B07C 5/342 |
| 2020/0281678 | A1 | 9/2020 | Long et al. | |
| 2022/0167987 | A1 | 6/2022 | Locke | |

FOREIGN PATENT DOCUMENTS

| | | | | |
|---|---|---|---|---|
| WO | 2020005062 | A1 | 1/2020 | |
| WO | WO-2020198484 | A1 * | 10/2020 | A61B 17/083 |

* cited by examiner

DEVICE FOR SKIN DISINFECTION AND ADHESIVE DEACTIVATION

CROSS-REFERENCE TO RELATED APPLICATIONS

This application is the United States national phase of International Application No. PCT/US2022/042286. Sep. 1, 2022, and claims priority to U.S. Provisional Application Ser. No. 63/240,029, entitled "Device for Skin Disinfection and Adhesive Deactivation", filed Sep. 2, 2021, the entire disclosures of which are hereby incorporated by reference in their entireties.

BACKGROUND

Intravenous (IV) therapy may refer to a medical technique that is used to deliver fluids, medications, and/or nutrition directly into a body of a patient via an IV line (e.g., an IV cannula, an IV catheter, etc.) inserted into a vein. IV therapy may be used for rehydration, to provide nutrition to a person who cannot consume food or water by mouth, and/or to administer medications or other medical therapy, such as blood products or electrolytes.

In some instances, an IV injection site for IV therapy may require a disinfection process. The disinfection process may involve the use of a topical disinfectant following removal of an IV dressing at the IV injection site. For example, the disinfection process for an IV injection site may be to remove an IV dressing covering the IV injection site and wiping down affected areas with a topical disinfectant, such as a wipe saturated with rubbing alcohol.

However, there may be significant drawbacks to removing the IV dressing that covers the IV injection site. For instance, removing the IV dressing may increase stress on the skin of a patient, which in many cases, in particular with elderly patients, may cause tearing and/or bruising of the skin. In addition, an IV line at the IV injection site may become dislodged from external or sub-dermal layers where the IV line enters into the skin.

Additionally, in some instances, securing the IV line may include the use of a backing material with an adhesive, such as tape, that is attached to the skin of the patient at or near an IV injection site to hold the IV line in place. Various adhesives may be used. Hydrocolloid and/or zinc oxide-based adhesives have less of a tendency to excoriate the skin of a patient when removed and that tendency may be particularly important for a patient whose skin is more sensitive or fragile. Hydrocolloid and/or zinc oxide-based adhesives may provide a low adhesion force between the adhesive and the skin, which allows minimal skin injury during a process of removing the adhesive from the skin.

However, it may also be important to minimize movement of components of the IV line, such as an IV catheter. In some instances, if the IV catheter is not properly secured in place, the IV catheter may be displaced from an intended location. Further, repeated movement of the IV catheter, to correctly position the IV catheter, can cause irritation of a blood vessel, disrupt proper introduction of medications to the patient, and/or increase the potential for bleeding or infection at the IV insertion site. If extensive movement occurs, the IV catheter could even come out of the patient, interrupting delivery of medication and requiring re-insertion, potentially with a requirement for hospitalization of the patient. Accordingly, a strong adhesion force between the adhesive and the skin may be desired to ensure secure positioning of the IV catheter during usage.

Therefore, there is an increasing need for disinfecting IV injection sites, including IV catheter insertion sites, without disturbing or providing minimal disturbance to the IV dressing that holds an IV line in place as well as that allows for removal of the IV line with minimal injury to the patient.

Such a disinfection device can also be useful for disinfecting other patient conditions with a dressing, such as, wound and surgery.

SUMMARY

Accordingly, provided are improved systems, devices, products, apparatus, and/or methods for a device for skin disinfection and adhesive deactivation.

According to some non-limiting embodiments or aspects, provided is a device comprising: a housing; a disinfecting light source coupled to the housing, wherein the disinfecting light source is configured to disinfect an object; an adhesive light source coupled to the housing, wherein the adhesive light source is configured to cause a light switchable adhesive to transition between an adhering state and a removal state based on the light switchable adhesive being exposed to light emitted by the adhesive light source; and an activation sensor coupled to the housing, wherein the activation sensor is electrically coupled to the disinfecting light source and the adhesive light source, and wherein the activation sensor is configured to cause the disinfecting light source and the adhesive light source to activate.

According to some non-limiting embodiments or aspects, provided is a device comprising: a housing; a disinfecting light source coupled to the housing, wherein the disinfecting light source is configured to disinfect an object; an adhesive light source coupled to the housing, wherein the adhesive light source is configured to cause a light switchable adhesive to transition between an adhering state and a removal state based on the light switchable adhesive being exposed to light emitted by the adhesive light source; and an activation sensor coupled to the housing, wherein the activation sensor is electrically coupled to the disinfecting light source and the adhesive light source, and wherein the activation sensor is configured to cause the disinfecting light source and the adhesive light source to activate; and a plurality of edge detection sensors, wherein each edge detection sensor of the plurality of edge detection sensors is configured to detect an edge of an object wherein the activation sensor is configured to: detect contact with a body of a user; and provide a signal to activate the disinfecting light source, the adhesive light source, or a combination of the disinfecting light source and the adhesive light source based on detecting contact the body of the user.

According to some non-limiting embodiments or aspects, provided is a assembly comprising: an intravenous (IV) injection site processing device comprising: a housing; a disinfecting light source coupled to the housing, wherein the disinfecting light source is configured to disinfect an object; an adhesive light source coupled to the housing, wherein the adhesive light source is configured to cause a light switchable adhesive to transition between an adhering state and a removal state based on the light switchable adhesive being exposed to light emitted by the adhesive light source; and an activation sensor coupled to the housing, wherein the activation sensor is electrically coupled to the disinfecting light source and the adhesive light source, and wherein the activation sensor is configured to cause the disinfecting light source and the adhesive light source to activate; and a securement device, wherein the IV injection site processing device is configured to be positioned to cover the securement device.

Further non-limiting embodiments or aspects are set forth in the following numbered clauses:

Clause 1: A device comprising: a housing; a disinfecting light source coupled to the housing, wherein the disinfecting light source is configured to disinfect an object; an adhesive light source coupled to the housing, wherein the adhesive light source is configured to cause a light switchable adhesive to transition between an adhering state and a removal state based on the light switchable adhesive being exposed to light emitted by the adhesive light source; and an activation sensor coupled to the housing, wherein the activation sensor is electrically coupled to the disinfecting light source and the adhesive light source, and wherein the activation sensor is configured to cause the disinfecting light source and the adhesive light source to activate.

Clause 2: The device of clause 1, wherein the disinfecting light source and the adhesive light source are configured to be activated based on a predetermined sequence.

Clause 3: The device of clauses 1 or 2, wherein the disinfecting light source or the adhesive light source is configured to be deactivated based on an expiration of a time interval.

Clause 4: The device of any of clauses 1-3, wherein the activation sensor is configured to: detect a presence of a body of a user; and provide a signal to activate the disinfecting light source, the adhesive light source, or a combination of the disinfecting light source and the adhesive light source based on detecting the presence of the body of the user.

Clause 5: The device of any of clauses 1-4, wherein the activation sensor is configured to: provide a signal to deactivate the disinfecting light source, the adhesive light source, or a combination of the disinfecting light source and the adhesive light source based on failing to detect the presence of the body of the user.

Clause 6: The device of any of clauses 1-5, wherein the adhesive light source provides light having a wavelength in a range of 315-400 nm.

Clause 7: The device of any of clauses 1-6, wherein the disinfecting light source provides light having a wavelength in a range of 405-470 nm.

Clause 8: The device of any of clauses 1-7, wherein the disinfecting light source or the adhesive light source comprises at least one light emitting diode (LED).

Clause 9: The device of any of clauses 1-8, further comprising a plurality of edge detection sensors, wherein each edge detection sensor of the plurality of edge detection sensors is configured to detect an edge of an object.

Clause 10: The device of any of clauses 1-9, wherein each edge detection sensor of the plurality of edge detection sensors is configured to provide an indication of a position of the object, and wherein the disinfecting light source and the adhesive light source are configured to be activated based on the position of the object.

Clause 11: The device of any of clauses 1-10, wherein each edge detection sensor is configured to detect the edge of the object based on color, texture, conductivity, and/or any combination thereof.

Clause 12: The device of any of clauses 1-11, wherein the housing comprises a base section and a plurality of support sections coupled to the base section, and wherein the base section and the plurality of support sections comprise a flexible material.

Clause 13: A device comprising: a housing; a disinfecting light source coupled to the housing, wherein the disinfecting light source is configured to disinfect an object; an adhesive light source coupled to the housing, wherein the adhesive light source is configured to cause a light switchable adhesive to transition between an adhering state and a removal state based on the light switchable adhesive being exposed to light emitted by the adhesive light source; and an activation sensor coupled to the housing, wherein the activation sensor is electrically coupled to the disinfecting light source and the adhesive light source, and wherein the activation sensor is configured to cause the disinfecting light source and the adhesive light source to activate; and a plurality of edge detection sensors, wherein each edge detection sensor of the plurality of edge detection sensors is configured to detect an edge of an object wherein the activation sensor is configured to: detect contact with a body of a user; and provide a signal to activate the disinfecting light source, the adhesive light source, or a combination of the disinfecting light source and the adhesive light source based on detecting contact the body of the user.

Clause 14: The device of clause 13, wherein each edge detection sensor of the plurality of edge detection sensors is configured to provide an indication of a position of the object, and wherein the disinfecting light source and the adhesive light source are configured to be activated based on the position of the object.

Clause 15: The device of clauses 13 or 14, wherein the disinfecting light source comprises at least one light emitting diode (LED) that provides light having a wavelength in a range of 405-470 nm and wherein the adhesive light source provides light having a wavelength in a range of 315-400 nm.

Clause 16: An assembly comprising: an intravenous (IV) injection site processing device comprising: a housing; a disinfecting light source coupled to the housing, wherein the disinfecting light source is configured to disinfect an object; an adhesive light source coupled to the housing, wherein the adhesive light source is configured to cause a light switchable adhesive to transition between an adhering state and a removal state based on the light switchable adhesive being exposed to light emitted by the adhesive light source; and an activation sensor coupled to the housing, wherein the activation sensor is electrically coupled to the disinfecting light source and the adhesive light source, and wherein the activation sensor is configured to cause the disinfecting light source and the adhesive light source to activate; and a securement device, wherein the IV injection site processing device is configured to be positioned to cover the securement device.

Clause 17: The assembly of clause 16, wherein the disinfecting light source comprises at least one light emitting diode (LED) that provides light having a wavelength in a range of 405-470 nm and wherein the adhesive light source comprises at least one light emitting diode (LED) that provides light having a wavelength in a range of 315-400 nm.

Clause 18: The assembly of clauses 16 or 17, wherein the securement device comprises the light switchable adhesive.

Clause 19: The assembly of any of clauses 16-18, wherein the light switchable adhesive is configured to transition between the adhering state and the removal state based on the light switchable adhesive being exposed to light provided by the adhesive light source.

Clause 20: The assembly of any of clauses 16-19, wherein the activation sensor is configured to: detect contact with a body of a user; and provide a signal to activate the disinfecting light source, the adhesive light source, or a combination of the disinfecting light source and the adhesive light source based on detecting contact the body of the user.

Clause 21: A device having a housing, a disinfecting light source coupled to the housing, wherein the disinfecting light source is configured to disinfect an object. The device further includes an activation sensor coupled to the housing, wherein the activation sensor is electrically coupled to the disinfecting light source, and wherein the activation sensor is configured to cause the disinfecting light source to activate. The device further includes a plurality of edge detection sensors, wherein each edge detection sensor of the plurality of edge detection sensors is configured to detect an edge of an object. The activation sensor is configured to detect contact with a body of a user, and provide a signal to activate the disinfecting light source, based on detecting contact the body of the user.

Clause 22: The device of clause 21, wherein each edge detection sensor of the plurality of edge detection sensors is configured to provide an indication of a position of the object, and wherein the disinfecting light source is configured to be activated based on the position of the object.

Clause 23: The device of any of clauses 21-22, wherein the disinfecting light source comprises at least one light emitting diode (LED) that provides light having a wavelength in a range of 405-470 nm.

Clause 24: A device including a housing, an adhesive light source coupled to the housing, wherein the adhesive light source is configured to cause a light switchable adhesive to transition between an adhering state and a removal state based on the light switchable adhesive being exposed to light emitted by the adhesive light source. The device also includes an activation sensor coupled to the housing, wherein the activation sensor is electrically coupled to the adhesive light source, and wherein the activation sensor is configured to cause the adhesive light source to activate. The device also includes a plurality of edge detection sensors, wherein each edge detection sensor of the plurality of edge detection sensors is configured to detect an edge of an object. The activation sensor is configured to detect contact with a body of a user, and provide a signal to activate the adhesive light source based on detecting contact the body of the user.

Clause 25: The device of any of clause 24, wherein each edge detection sensor of the plurality of edge detection sensors is configured to provide an indication of a position of the object, and wherein the adhesive light source is configured to be activated based on the position of the object.

Clause 26: The device of any of clauses 24-25, wherein the adhesive light source provides light having a wavelength in a range of 315-400 nm.

BRIEF DESCRIPTION OF THE DRAWINGS

Additional advantages and details are explained in greater detail below with reference to the exemplary embodiments that are illustrated in the accompanying schematic figures, in which.

DETAILED DESCRIPTION

Figure 1:
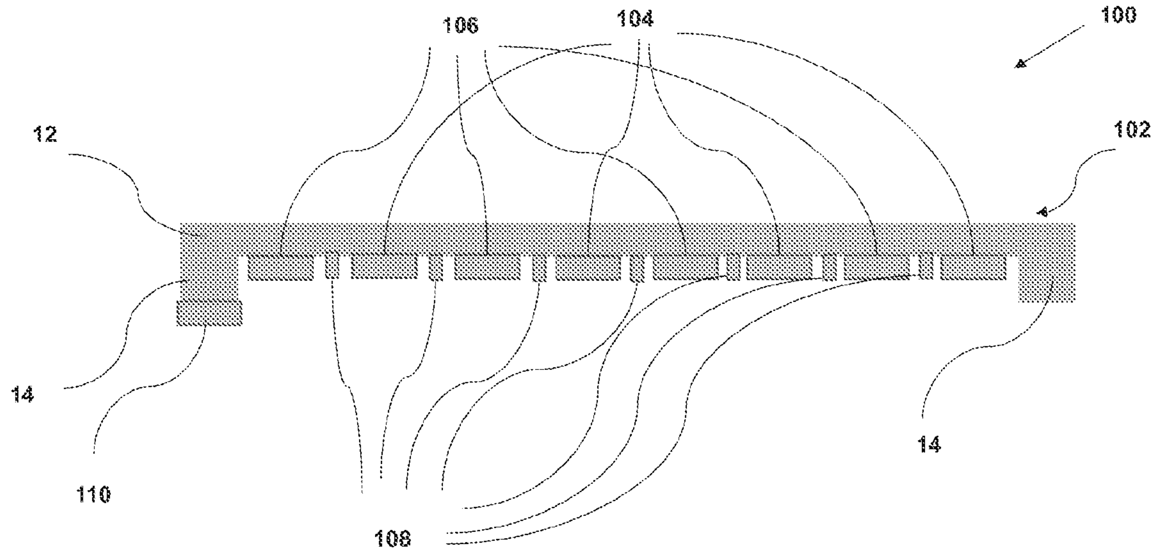
FIG. 1 is a diagram of a non-limiting embodiment of an IV injection site processing device.

It is to be understood that the present disclosure may assume various alternative variations and step sequences, except where expressly specified to the contrary. It is also to be understood that the specific devices and processes illustrated in the attached drawings, and described in the following specification, are simply exemplary and non-limiting embodiments or aspects. Hence, specific dimensions and other physical characteristics related to the embodiments or aspects disclosed herein are not to be considered as limiting.

For purposes of the description hereinafter, the terms "end," "upper," "lower," "right," "left," "vertical," "horizontal," "top," "bottom," "lateral," "longitudinal," and derivatives thereof shall relate to embodiments or aspects as they are oriented in the drawing figures. However, it is to be understood that embodiments or aspects may assume various alternative variations and step sequences, except where expressly specified to the contrary. It is also to be understood that the specific devices and processes illustrated in the attached drawings, and described in the following specification, are simply non-limiting exemplary embodiments or aspects. Hence, specific dimensions and other physical characteristics related to the embodiments or aspects of the embodiments or aspects disclosed herein are not to be considered as limiting unless otherwise indicated.

No aspect, component, element, structure, act, step, function, instruction, and/or the like used herein should be construed as critical or essential unless explicitly described as such. Also, as used herein, the articles "a" and "an" are intended to include one or more items, and may be used interchangeably with "one or more" and "at least one." As used in the specification and the claims, the singular form of "a," "an," and "the" include plural referents, such as unless the context clearly dictates otherwise. Additionally, Furthermore, as used herein, the terms "set" and "group" are intended to include one or more items (e.g., related items, unrelated items, a combination of related and unrelated items, etc.) and may be used interchangeably with "one or more" or "at least one." Where only one item is intended, the term "one" or similar language is used. Also, as used herein, the terms "has," "have," "having," or the like are intended to be open-ended terms. Further, the phrase "based on" is intended to mean "based at least partially on" unless explicitly stated otherwise. Further, the phrase "based on" may mean "in response to" and be indicative of a condition for automatically triggering a specified operation of an electronic device (e.g., a controller, a processor, a computing device, etc.) as appropriately referred to herein.

Some non-limiting embodiments or aspects may be described herein in connection with thresholds. As used herein, satisfying a threshold may refer to a value being greater than the threshold, more than the threshold, higher than the threshold, greater than or equal to the threshold, less than the threshold, fewer than the threshold, lower than the threshold, less than or equal to the threshold, equal to the threshold, etc.

According to embodiments of the present disclosure, an intravenous (IV) injection site processing device may include a housing, a disinfecting light source coupled to the housing, where the disinfecting light source is configured to disinfect an object, an adhesive light source coupled to the housing, where the adhesive light source is configured to cause a light switchable adhesive to transition between an adhering state and a removal state based on the light switchable adhesive being exposed to light emitted by the adhesive light source, and an activation sensor coupled to the housing, wherein the activation sensor is electrically coupled to the disinfecting light source and the adhesive light source, and wherein the activation sensor is configured to cause the disinfecting light source and the adhesive light source to activate. In some non-limiting embodiments, the disinfecting light source and the adhesive light source are configured to be activated based on a predetermined sequence. In some non-limiting embodiments, the disinfecting light source or the adhesive light source is configured to be deactivated based on an expiration of a time interval. In some non-limiting embodiments, the activation sensor is configured to: detect a presence of a body of a user, and provide a signal to activate the disinfecting light source, the adhesive light source, or a combination of the disinfecting light source and the adhesive light source based on detecting the presence body of the user. In some non-limiting embodiments, the activation sensor is configured to provide a signal to deactivate the disinfecting light source, the adhesive light source, or a combination of the disinfecting light source and the adhesive light source based on failing to detect the presence of the body of the user. In some non-limiting embodiments, the adhesive light source provides light having a wavelength in a range of 315-400 nm. In some non-limiting embodiments, the disinfecting light source provides light having a wavelength in a range of 405-470 nm. In some non-limiting embodiments, the disinfecting light source or the adhesive light source comprises at least one LED. In some non-limiting embodiments, the IV injection site processing device further comprises a plurality of edge detection sensors, where each edge detection sensor of the plurality of edge detection sensors is configured to detect an edge of an object. In some non-limiting embodiments, each edge detection sensor of the plurality of edge detection sensors is configured to provide an indication of a position of the object, and the disinfecting light source and the adhesive light source are configured to be activated based on the position of the object. In some non-limiting embodiments, each edge detection sensor is configured to detect the edge of the object based on color, texture, conductivity, and/or any combination thereof. In some non-limiting embodiments, the housing comprises a base section and a plurality of support sections coupled to the base section, and wherein the base section and the plurality of support sections comprise a flexible material.

In some non-limiting embodiments, an IV injection site processing device may include a housing, a disinfecting light source coupled to the housing, where the disinfecting light source is configured to disinfect an object, an adhesive light source coupled to the housing, where the adhesive light source is configured to cause a light switchable adhesive to transition between an adhering state and a removal state based on the light switchable adhesive being exposed to light emitted by the adhesive light source, an activation sensor coupled to the housing, wherein the activation sensor is electrically coupled to the disinfecting light source and the adhesive light source, and wherein the activation sensor is configured to cause the disinfecting light source and the adhesive light source to activate, and a plurality of edge detection sensors, where each edge detection sensor of the plurality of edge detection sensors is configured to detect an edge of an object, where the activation sensor is configured to detect contact with a body of a user, and provide a signal to activate the disinfecting light source, the adhesive light source, or a combination of the disinfecting light source and the adhesive light source based on detecting contact the body of the user. In some non-limiting embodiments, each edge detection sensor of the plurality of edge detection sensors is configured to provide an indication of a position of the object, and the disinfecting light source and the adhesive light source are configured to be activated based on the position of the object. In some non-limiting embodiments, the disinfecting light source comprises at least one LED that provides light having a wavelength in a range of 405-470 nm and wherein the adhesive light source provides light having a wavelength in a range of 315-400 nm.

In some non-limiting embodiments, an IV injection site assembly may include an IV injection site processing device and a securement device. The IV injection site processing device may include a housing, a disinfecting light source coupled to the housing, where the disinfecting light source is configured to disinfect an object, an adhesive light source coupled to the housing, wherein the adhesive light source is configured to cause a light switchable adhesive to transition between an adhering state and a removal state based on the light switchable adhesive being exposed to light emitted by the adhesive light source, and an activation sensor coupled to the housing, wherein the activation sensor is electrically coupled to the disinfecting light source and the adhesive light source, and wherein the activation sensor is configured to cause the disinfecting light source and the adhesive light source to activate, and the IV injection site processing device is configured to be positioned to cover the securement device. In some non-limiting embodiments, the disinfecting light source comprises at least one LED that provides light having a wavelength in a range of 405-470 nm and wherein the adhesive light source comprises at least one LED that provides light having a wavelength in a range of 315-400 nm. In some non-limiting embodiments, the securement device comprises the light switchable adhesive. In some non-limiting embodiments, the light switchable adhesive is configured to transition between the adhering state and the removal state based on the light switchable adhesive being exposed to light provided by the adhesive light source. In some non-limiting embodiments, the activation sensor is configured to detect contact with a body of a user; and provide a signal to activate the disinfecting light source, the adhesive light source, or a combination of the disinfecting light source and the adhesive light source based on detecting contact the body of the user.

In this way, embodiments of the present disclosure allow for an IV injection site processing device that disinfects IV injection sites, including IV catheter insertion sites, without disturbing any devices used at the IV injection sites, such as an IV dressing that holds an IV line in place, and that allows for removal of the IV injection site stabilization device and/or the IV line with no or minimal disturbance to the patient once the IV line is to be repositioned or is no longer necessary.

Referring now to FIG. 1, FIG. 1 is a diagram of intravenous (IV) injection site processing device 100 and components thereof. As shown in FIG. 1, IV injection site processing device 100 may include housing 102, disinfecting light source 104, adhesive light source 106, edge detection sensors 108, and activation sensor 110. As shown in FIG. 1, housing 102 may include base section 112 and support sections 114 that are coupled to (e.g., formed on) base section 112 and extend away from base section 112. In some non-limiting embodiments, support sections 114 are configured to contact an object, such as skin of a user, and allow for disinfecting light source 104, adhesive light source 106, and/or edge detection sensors 108 to be positioned a distance away from the object.

In some non-limiting embodiments, housing 102 may have a concave shape. In this way, IV injection site processing device 100 may be used to cover an IV injection site, such as an IV catheter insertion site, to provide a barrier to contamination of the IV injection site as well as providing light (e.g., in the form of electromagnetic radiation) that disinfects an object (e.g., a surface of an object) covered by IV injection site processing device 100 and/or is configured to cause a light switchable adhesive to transition between the adhering state and the removal state. In some non-limiting embodiments, housing 102 may be sized and configured so that IV injection site processing device 100 is a wearable device. For example, housing 102 may have a form factor so that IV injection site processing device 100 is wearable on a body of a user. Additionally or alternatively, IV injection site processing device 100 may include an attachment mechanism to secure IV injection site processing device 100 to a body of a user. For example, IV injection site processing device 100 may include an adhesive (e.g., an adhesive around an edge of housing 102), a strap, a band, a belt, a hook and loop fastener, a wrap, a clip, a clamp, and/or the like, that would allow IV injection site processing device 100 to be worn by a user.

In some non-limiting embodiments, base section 112 and/or support sections 114 of housing 102 may include (e.g., may be constructed of) a flexible material so that housing 102 may conform to an object (e.g., a surface of an object, such as a body of a user) to which IV injection site processing device 100 may be applied. For example, base section 112 and/or support sections 114 of housing 102 may include a polymer, such as a plastic and/or rubber. Additionally or alternatively, base section 112 and/or support sections 114 of housing 102 may include polymer foam such as a flexible polymeric foam. The polymer foam can be based on polyurethane, polyethylene and copolymer, and/or polypropylene, for example. In some non-limiting embodiments, a material for housing 102 may include plastics such as rigid plastics, semi-rigid plastics, and/or the like. Additionally or alternatively, the material may include rubbers and elastomers. The plastics may include low density polyethylene, high density polyethylene, polyethylene copolymers, polypropylene and its copolymer, polyvinyl chloride, polymer styrene and its copolymers, nylon, acrylic polymers, polycarbonate, polyester, thermoplastic elastomers, and the polymer blends and polymer composites.

In some non-limiting embodiments, base section 112 and support sections 114 of housing 102 may be formed as a unitary component (e.g., as a single piece). For example, base section 112 and support sections 114 of housing 102 may be molded (e.g., injection molded) as a unitary component. In some non-limiting embodiments, support sections 114 may be attached to base section 112 as part of a process of forming housing 102. It is further contemplated herein that the housing 102 may be a flexible membrane.

In some non-limiting embodiments, disinfecting light source 104 may include one or more devices (e.g., light elements) that are configured to provide light that disinfects an object. For example, disinfecting light source 104 may include one or more devices that is configured to provide light having a wavelength that disinfects the object. In this way, IV injection site processing device 100 may provide for disinfection (e.g., antimicrobial disinfection) of an object (e.g., a surface of object at an IV injection site), such as skin of an appendage (e.g., an arm and/or a leg) of a user based on the use of disinfecting light source 104. In addition, IV injection site processing device 100 may reduce infection at the site of a user on which IV injection site processing device 100 is applied. In some non-limiting embodiments, disinfecting light source 104 may include one or more light elements, where each light element may include a light emitting diode (LED), a light bulb, a light-emitting electrochemical cell (LEC), a laser, and/or the like. In some non-limiting embodiments, disinfecting light source 104 may be coupled to housing 102. For example, one or more light elements of disinfecting light source 104 may be attached to base section 112 of housing 102.

In some non-limiting embodiments, disinfecting light source 104 may provide antimicrobial blue light (aBL), which may include electromagnetic radiation having a wavelength between 400-470 nm. Additionally or alternatively, disinfecting light source 104 may provide electromagnetic radiation having a wavelength between 630-680 nm, which may be referred to as red light. Additionally or alternatively, disinfecting light source 104 may provide electromagnetic radiation having a wavelength between 10-400 nm, which may include electromagnetic radiation in the ultraviolet (UV) spectrum. For example, disinfecting light source 104 may provide electromagnetic radiation having a wavelength between 100-280 nm (e.g., the UVC spectrum), electromagnetic radiation having a wavelength between 280-315 nm (e.g., the UVB spectrum), and/or electromagnetic radiation having a wavelength between 315-400 nm (e.g., the UVA spectrum).

In some non-limiting embodiments, adhesive light source 106 may include one or more devices (e.g., light elements) that are configured to provide a light that causes a light switchable adhesive to transition between an adhering state and a removal state. For example, adhesive light source 106 may include one or more devices that is configured to provide light having a wavelength that is configured to cause a light switchable adhesive to transition from the adhering state to the removal state. In this way, IV injection site processing device 100 may allow for deactivation of light switchable adhesive and therefore, may minimize injury to a patient during removal of components associated with an IV line. In some non-limiting embodiments, adhesive light source 106 may include one or more devices that are configured to cause the light switchable adhesive to transition from the adhering state to the removal state only. For example, adhesive light source 106 may include one or more devices that are configured to emit light having a wavelength that causes the light switchable adhesive to transition from the adhering state to the removal state but adhesive light source 106 may forego one or more devices that are configured to emit light having a wavelength that causes the light switchable adhesive to transition from the removal state to the adhering state. In some non-limiting embodiments, adhesive light source 106 may include one or more devices that are configured to cause the light switchable adhesive to transition from the removal state to the adhering state only. For example, adhesive light source 106 may include one or more devices that are configured to emit light having a wavelength that causes the light switchable adhesive to transition from the removal state to the adhering state but adhesive light source 106 may forego one or more devices that are configured to emit light having a wavelength that causes the light switchable adhesive to transition from the adhering state to the removal state.

In some non-limiting embodiments, a light switchable adhesive may include an adhesive configured to transition between an adhering state and a removal state based on exposure of the light switchable adhesive to light (e.g., electromagnetic radiation having a specific wavelength). For example, the light switchable adhesive may include an adhesive that is configured to transition between the adhering state and the removal state based on the light switchable adhesive being exposed to light having a specific wavelength. In some non-limiting embodiments, the light switchable adhesive may be configured to transition between the adhering state and the removal state based on the light switchable adhesive being exposed to ultraviolet light (e.g., electromagnetic radiation having a wavelength in a range between 100-400 nm). In some non-limiting embodiments, the light switchable adhesive may be configured to transition between the adhering state and the removal state based on being exposed to light having a wavelength in a range between 100-280 nm (e.g., in the UVC spectrum), light having a wavelength in a range between 280-315 nm (e.g., in the UVB spectrum), and/or light having a wavelength in a range between 315-400 nm (e.g., in the UVA spectrum).

In some non-limiting embodiments, a light switchable adhesive may have an adhering state and a removal state. An amount of force with which the light switchable adhesive adheres to an object (e.g., an amount of force that is required to remove the switchable adhesive from an object) in the adhering state is greater than an amount of force with which the light switchable adhesive adheres to an object in the removal state. For example, the amount of force with which the light switchable adhesive adheres to an object in the removal state may be at least 30% less than the amount of force with which the light switchable adhesive adheres to an object in the adhering state.

In some non-limiting embodiments, adhesive light source 106 may include one or more light elements, where each light element may include a light emitting diode (LED), a light bulb, a light-emitting electrochemical cell (LEC), a laser, and/or the like. In some non-limiting embodiments, adhesive light source 106 may be coupled to housing 102. For example, one or more light elements of adhesive light source 106 may be attached to base section 112 of housing 102.

In some non-limiting embodiments, adhesive light source 106 may provide antimicrobial blue light (aBL), which may include electromagnetic radiation having a wavelength between 400-470 nm. Additionally or alternatively, adhesive light source 106 may provide electromagnetic radiation having a wavelength between 630-680 nm, which may be referred to as red light. Additionally or alternatively, adhesive light source 106 may provide electromagnetic radiation having a wavelength between 10-400 nm, which may include electromagnetic radiation in the ultraviolet (UV) spectrum. For example, adhesive light source 106 may provide electromagnetic radiation having a wavelength between 100-280 nm (e.g., the UVC spectrum), electromagnetic radiation having a wavelength between 280-315 nm (e.g., the UVB spectrum), and/or electromagnetic radiation having a wavelength between 315-400 nm (e.g., the UVA spectrum).

In some non-limiting embodiments, disinfecting light source 104 and/or adhesive light source 106 may be configured to be in contact (e.g., in physical contact) with an object covered by IV injection site processing device 100. For example, one or more light elements of disinfecting light source 104 and/or one or more light elements of adhesive light source 106 may be configured to be in contact with the object covered by IV injection site processing device 100. In some non-limiting embodiments, one or more light elements of disinfecting light source 104 and/or one or more light elements of adhesive light source 106 may be attached to a printed circuit board (PCB) and the PCB may be couple to (e.g., attached to) housing 102.

In some non-limiting embodiments, disinfecting light source 104 may provide light having a first wavelength (e.g., light having a first wavelength within a first range of wavelengths) and adhesive light source 106 may provide light having a second wavelength (e.g., light having a second wavelength within a second range of wavelengths). In some non-limiting embodiments, the first wavelength and the second wavelength may not overlap. In this way, IV injection site processing device 100 may perform the two separate processes of disinfection and adhesive deactivation or activation without one process affecting the other based on exposure of light having a wavelength that would otherwise cause both processes to happen simultaneously. In one example, disinfecting light source 104 may provide light having a first wavelength centered around 405 nm or above, and adhesive light source 106 may provide light having a second wavelength centered around 365 nm. In another example, disinfecting light source 104 may provide light having a wavelength in a range of 405-470 nm and/or adhesive light source 106 may provide light having a wavelength in a range of 315-400 nm.

Figure 2:
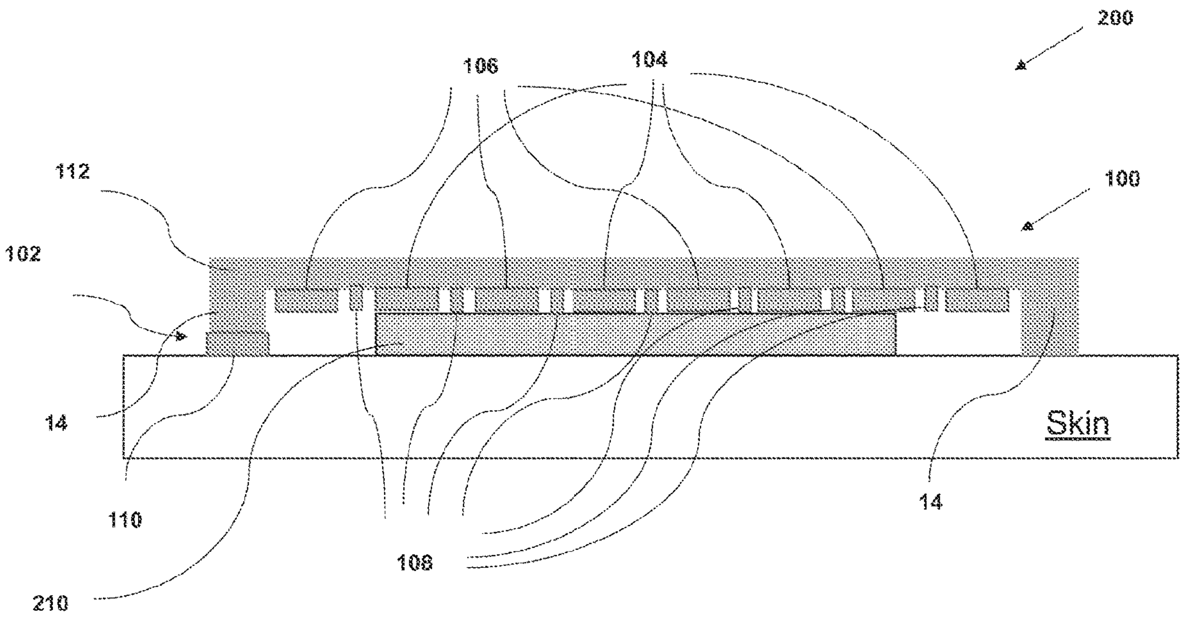
FIG. 2 is a diagram of an IV injection site assembly, including a securement device and the IV injection site processing device shown in FIG. 1 in contact with the skin of a user.

In some non-limiting embodiments, edge detection sensor 108 may include one or more devices that are configured to detect an edge, such as an edge of an object, an edge of a surface of an object, and/or the like. For example, edge detection sensor 108 may include one or more devices that are configured to detect an edge of an object which is covered by IV injection site processing device 100. In some non-limiting embodiments, edge detection sensor 108 may detect the edge of an object based on color, texture, and/or conductivity (e.g., a difference in conductivity). In some non-limiting embodiments, edge detection sensor 108 may include one or more photoelectric sensors, one or more laser sensors, one or more ultrasonic sensors, one or more color sensors, one or more contact sensors, one or more proximity sensors, one or more image sensors, and/or the like. In some non-limiting embodiments, IV injection site processing device 100 may include one or more edge detection sensors 108. As shown in FIGS. 1 and 2, IV injection site processing device 100 may include a plurality of edge detection sensors 108. In some non-limiting embodiments, each edge detection sensor 108 of a plurality of edge detection sensors 108 may be placed at regular intervals of distance outward (e.g., outward towards support sections 114 of housing 102) from a center point of base section 112 of housing 102. In some non-limiting embodiments, edge detection sensors 108 may be positioned adjacent each light element of disinfecting light source 104 and adhesive light source 106. In one example, one edge detection sensor 108 may be positioned between two light elements (e.g., between one light element of disinfecting light source 104 and one light element of adhesive light source 106, between two light elements of disinfecting light source 104, between two light elements of adhesive light source 106, etc.).

In some non-limiting embodiments, disinfecting light source 104 and/or adhesive light source 106 may be controlled based on one or more edge detection sensors 108. For example, a controller (not shown) may receive a signal from one or more edge detection sensors 108 and the controller may cause one or more light elements of disinfecting light source 104 and/or one or more light elements of adhesive light source 106 to activate based on the signal received from the one or more edge detection sensors 108. In some non-limiting embodiments, disinfecting light source 104 and/or adhesive light source 106 may be controlled based on an object detected by one or more edge detection sensors 108. For example, the controller may receive a signal from one or more edge detection sensors 108 that indicates a position of the object. The position of the object may define a surface area (e.g., an amount of space taken up by the object, a footprint of the object, etc.) of the object as detected by the one or more edge detection sensors 108. The controller may cause (e.g., only cause) one or more light elements of disinfecting light source 104 and/or one or more light elements of adhesive light source 106 to activate that correspond to the position of the object (e.g., that are within the surface area of the object as detected by the one or more edge detection sensors 108) based on the signal. In such an example, the controller may forego causing one or more light elements of disinfecting light source 104 and/or one or more light elements of adhesive light source 106 to activate that do not correspond to the position of the object. In some non-limiting embodiments, the controller may cause (e.g., only cause) one or more light elements of disinfecting light source 104 and/or one or more light elements of adhesive light source 106 to deactivate that do not correspond to the position of the object based on the signal. In some non-limiting embodiments, one or more light elements of disinfecting light source 104 and/or one or more light elements of adhesive light source 106 that correspond to the position of the object may be selectively activated. For example, the controller may cause (e.g., only cause) one or more light elements of disinfecting light source 104 and/or one or more light elements of adhesive light source 106 that correspond to the position of the object to activate based on a predetermined sequence, a user input, a time interval, and/or any combination thereof.

As referred to herein, a controller may include a device configured to control disinfecting light source 104 and/or adhesive light source 106. For example, the controller may include a device configured to control (e.g., control the activation and/or deactivation of) disinfecting light source 104 and/or adhesive light source 106 based on information received from one or more edge detection sensors 108 and/or activation sensor 110. In some non-limiting embodiments, the controller may include a processor, such as a central processing unit (CPU), a microcontroller, an integrated circuit (IC), and/or the like. In some non-limiting embodiments, the controller may include a switch device, such as an electrical switch.

In some non-limiting embodiments, a contact sensor may include a device that is configured to detect contact with a body of a user of IV injection site processing device 100. In some non-limiting embodiments, the contact sensor may include a touch sensor, such as a capacitive touch sensor, a resistive touch sensor, and/or the like. In some non-limiting embodiments, the contact sensor may include a plurality of electrical circuit components (e.g., a plurality of electrical traces, a plurality of electrical contacts, a plurality of electrodes, etc.). In some non-limiting embodiments, the contact sensor may include a sensor (e.g., a sensor of a controller) in electrical contact with the plurality of electrical traces, and the sensor may be configured to determine whether a conductive path is present from a first electrical circuit component of the plurality of electrical circuit components to a second electrical circuit component of the plurality of electrical circuit components. In some non-limiting embodiments, the contact sensor may include a first electrical circuit component and a second electrical circuit component, where the first electrical circuit component and the second electrical circuit component are separated by a gap. In some non-limiting embodiments, the contact sensor may detect contact with the body of the user based on a reduction in resistance between the first electrical circuit component and the second electrical circuit component when the first electrical circuit component and the second electrical circuit component are in electrical contact with the body of the user. In this way, the contact sensor may detect contact with the body of the user based on the body of the user providing a conductive path over the gap between the first electrical circuit component and the second electrical circuit component.

In some non-limiting embodiments, a proximity sensor may include a device configured to detect whether the proximity sensor is in proximity (e.g., satisfies a condition of being near) to an object, such as a body (e.g., an appendage of a body) of a user. In some non-limiting embodiments, the proximity sensor may be configured to detect when the proximity sensor is within a predetermined threshold of distance to the object. In some non-limiting embodiments, the proximity sensor may include an inductive proximity sensor, an optical proximity sensor, capacitive proximity sensor, magnetic proximity sensor, ultrasonic proximity sensor, and/or the like.

In some non-limiting embodiments, activation sensor 110 may include one or more devices that are configured to detect contact with an object (e.g., a body of a user, an appendage of a body of a user, skin of a user, etc.) by activation sensor 110 and/or whether an object is in proximity to activation sensor 110. For example, activation sensor 110 may include one or more devices that are configured to detect contact with an object by activation sensor 110 and/or whether an object is in proximity to activation sensor 110, where the object is an object upon which IV injection site processing device 100 is positioned. In some non-limiting embodiments, activation sensor 110 may include one or more photoelectric sensors, one or more laser sensors, one or more ultrasonic sensors, one or more color sensors, one or more contact sensors, one or more proximity sensors, one or more image sensors, and/or the like. In some non-limiting embodiments, activation sensor 110 may include a switch device, such as an electrical switch.

In some non-limiting embodiments, activation sensor 110 may detect a presence of an object (e.g., a body of a user) and provide a signal to activate disinfecting light source 104 and/or adhesive light source 106 based on detecting the presence of the object. In some non-limiting embodiments, activation sensor 110 may provide a signal to deactivate disinfecting light source 104 and/or adhesive light source 106 based on failing to detect the presence of the object. In some non-limiting embodiments, activation sensor 110 may forego providing a signal based on failing to detect the presence of the object. In some non-limiting embodiments, a controller may deactivate disinfecting light source 104 and/or adhesive light source 106 based on failing to receive the signal from activation sensor 110.

In some non-limiting embodiments, disinfecting light source 104 and/or adhesive light source 106 may be controlled based on activation sensor 110. For example, a controller (not shown) may receive a signal from activation sensor 110 and the controller may cause one or more light elements of disinfecting light source 104 and/or one or more light elements of adhesive light source 106 to activate based on the signal received from activation sensor 110. In some non-limiting embodiments, disinfecting light source 104 and/or adhesive light source 106 may be controlled based on activation sensor 110 detecting contact with an object by activation sensor 110 and/or that an object is in proximity to activation sensor 110. For example, the controller may receive a signal from activation sensor 110 that indicates that activation sensor 110 is in contact with the object and/or that the object is in proximity to activation sensor 110. The controller may cause one or more light elements of disinfecting light source 104 and/or one or more light elements of adhesive light source 106 to activate based on the signal from activation sensor 110. In some non-limiting embodiments, disinfecting light source 104 and/or adhesive light source 106 may be controlled based on activation sensor 110 not detecting contact with an object by activation sensor 110 and/or that an object is not in proximity to activation sensor 110. For example, the controller may not receive a signal from activation sensor 110 that indicates that activation sensor 110 is in contact with the object and/or that the object is in proximity to activation sensor 110. The controller may forgo causing one or more light elements of disinfecting light source 104 and/or one or more light elements of adhesive light source 106 to activate based on the controller not receiving the signal from activation sensor 110. In this way, activation sensor 110 may allow for disinfecting light source 104 and/or adhesive light source 106 of IV injection site processing device 100 to be activated only when activation sensor 110 detects that activation sensor is in contact with a body of a user and/or that the body of the user is in proximity to activation sensor 110. Accordingly, activation sensor 110 may allow for the conservation of power by preventing activation of disinfecting light source 104 and/or adhesive light source 106 and activation sensor 110 may prevent unintentional exposure of light provided by disinfecting light source 104 and/or adhesive light source 106.

In some non-limiting embodiments, disinfecting light source 104 and/or adhesive light source 106 may be controlled based on activation sensor 110 and one or more edge detection sensors 108. In one example, a controller may prevent the one or more edge detection sensors 108 from detecting a position of a first object unless a signal is received from activation sensor 110 that indicates that activation sensor 110 is in contact with a second object and/or that the second object is in proximity to activation sensor 110. The first object may be a securement device and the second object may be a body of a user. In such an example, the controller may cause the one or more edge detection sensors 108 to detect the position of the first object based on receiving the signal from activation sensor 110 that indicates that activation sensor 110 is in contact with the second object and/or that the second object is in proximity to activation sensor 110. Further, the disinfecting light source 104 and/or adhesive light source 106 may be controlled according to a signal received from the one or more edge detection sensors 108 that indicates a position of the first object. The controller may cause one or more light elements of disinfecting light source 104 and/or one or more light elements of adhesive light source 106 to activate that correspond to the position of the object based on the signal. Additionally or alternatively, the controller may forego causing one or more light elements of disinfecting light source 104 and/or one or more light elements of adhesive light source 106 to activate that do not correspond to the position of the object.

In some non-limiting embodiments, disinfecting light source 104 and/or adhesive light source 106 may be controlled based on a time interval (e.g., a predetermined time interval, a time interval associated with a disinfection process, a time interval associated with an adhesive activation or deactivation process, etc.). In one example, a controller may cause one or more light elements of disinfecting light source 104 and/or one or more light elements of adhesive light source 106 to activate based on an initiation of the time interval (e.g., based on the activation of a time counter for the time interval). Additionally or alternatively, the controller may cause one or more light elements of disinfecting light source 104 and/or one or more light elements of adhesive light source 106 to deactivate based on an expiration of the time interval. In some non-limiting embodiments, disinfecting light source 104 and/or adhesive light source 106 may be configured to be deactivated based on an expiration of the time interval. In some non-limiting embodiments, the time interval may be selected by a user of IV injection site processing device 100 (e.g., a patient, a doctor, etc.). For example, the time interval may be selected by the user via a user input device, such as a physical component (e.g., a dial, a switch, a button, etc.) or a user interface (e.g., a graphical user interface, an element of a user interface, etc.). In some non-limiting embodiments, the time interval may be a predetermined time interval (e.g., a preprogrammed time interval) that is stored in a memory of IV injection site processing device 100 and that is retrieved by a controller prior to activation of disinfecting light source 104 and/or adhesive light source 106.

In some non-limiting embodiments, disinfecting light source 104 and/or adhesive light source 106 may be controlled based on a time interval and activation sensor 110 and/or one or more edge detection sensors 108. For example, a controller may prevent the initiation of the time interval (e.g., the time interval during which disinfecting light source 104 and/or adhesive light source 106 is activated) unless a signal is received from activation sensor 110 that indicates that activation sensor 110 is in contact with an object and/or that the object is in proximity to activation sensor 110. In some non-limiting embodiments, the controller may initiate the time interval based on receiving the signal from activation sensor 110 that indicates that activation sensor 110 is in contact with an object and/or that the object is in proximity to activation sensor 110. In another example, the controller may prevent the initiation of the time interval unless a signal is received from the one or more edge detection sensors 108 that indicates a position of an object detected by the one or more edge detection sensors 108. In some non-limiting embodiments, the controller may initiate the time interval based on receiving the signal from the one or more edge detection sensors 108 that indicates the position of the object detected by the one or more edge detection sensors 108. In some non-limiting embodiments, the controller may prevent the initiation of the time interval unless the signal is received from activation sensor 110 that indicates that activation sensor 110 is in contact with a first object and/or that the first object is in proximity to activation sensor 110 and the signal is received from the one or more edge detection sensors 108 that indicates the position of a second object detected by the one or more edge detection sensors 108. In some non-limiting embodiments, the controller may initiate the time interval based on receiving the signal from activation sensor 110 that indicates that activation sensor 110 is in contact with the first object and/or that the first object is in proximity to activation sensor 110 and the signal from the one or more edge detection sensors 108 that indicates the position of the second object detected by the one or more edge detection sensors 108.

In some non-limiting embodiments, disinfecting light source 104 and adhesive light source 106 may be controlled based on different time intervals. For example, the controller may cause one or more light elements of disinfecting light source 104 to activate based on a first time interval and the controller may cause one or more light elements of adhesive light source 106 to activate based on a second time interval, where the first time interval and the second time interval are different. In some non-limiting embodiments, the first time interval for disinfecting light source 104 may be longer than the second time interval for adhesive light source 106. In this way, a disinfection process may be properly performed using disinfecting light source 104 and an adhesive deactivation or activation process may be properly performed using adhesive light source 106. In one example, the first time interval may be equal to or greater than 10 minutes and the second time interval may be equal to or less than 5 minutes.

In some non-limiting embodiments, disinfecting light source 104 and/or adhesive light source 106 may be controlled based on a plurality of time intervals. For example, a controller may cause one or more light elements of disinfecting light source 104 and/or one or more light elements of adhesive light source 106 to activate based on an initiation of a time interval at one or more regularly scheduled time intervals. In one such example, the controller may cause one or more light elements of disinfecting light source 104 to activate based on the initiation of a time interval for a disinfection process (e.g., a time interval of 10 minutes or more, such as 25 minutes) at a regularly scheduled time interval of every 12 hours. In some non-limiting embodiments, the regularly scheduled time interval may be for a predetermined amount of time, such as a day, a week, a month, and/or the like.

In some non-limiting embodiments, disinfecting light source 104 and/or adhesive light source 106 may be controlled based on a predetermined sequence. For example, one or more light elements of disinfecting light source 104 and one or more light elements of adhesive light source 106 may be activated and/or deactivated based on the predetermined sequence. In some non-limiting embodiments, disinfecting light source 104 may be activated and adhesive light source 106 may be activated after disinfecting light source 104 is activated. In some non-limiting embodiments, disinfecting light source 104 and/or adhesive light source 106 may be controlled based on an input from a user. For example, one or more light elements of disinfecting light source 104 and one or more light elements of adhesive light source 106 may be activated based on the input from the user. In some non-limiting embodiments, the input from the user may overwrite a predetermined sequence during which disinfecting light source 104 and/or adhesive light source 106 may be activated. For example, one or more light elements of disinfecting light source 104 and one or more light elements of adhesive light source 106 may be activated based on the predetermined sequence and during the predetermined sequence, an input from the user is received. The input from the user may interrupt the predetermined sequence and the one or more light elements of disinfecting light source 104 and one or more light elements of adhesive light source 106 may be activated based on the input from the user.

Referring now to FIG. 2, FIG. 2 is a diagram of IV injection site assembly 200, including securement device 210 and IV injection site processing device 100. As shown in FIG. 2, IV injection site processing device 100 may be placed over top of securement device 210 and securement device 210 may be attached to the skin of a user.

In some non-limiting embodiments, securement device 210 may include a retaining mechanism (e.g., a retainer, a lock, a clip, a hook, a clamp, an anchor, etc.) for holding a component of an IV line. For example, securement device 210 may include a catheter retainer. In another example, the securement device may include a catheter securement pad. In some non-limiting embodiments, securement device 210 may include a medical device for treating a user of IV injection site processing device 100. For example, securement device 210 may include a wound dressing. In some non-limiting embodiments, securement device 210 may include a layer of a light switchable adhesive to adhere to the skin of the user.

In some non-limiting embodiments, the light switchable adhesive is configured to transition between the adhering state and the removal state based on the light switchable adhesive being exposed to light having a specific wavelength provided by adhesive light source 106. In some non-limiting embodiments, the light switchable adhesive is configured to transition between the adhering state and the removal state based on the light switchable adhesive being exposed to ultraviolet light (e.g., electromagnetic radiation having a wavelength in a range between 100-400 nm). In some non-limiting embodiments, the light switchable adhesive is configured to transition between the adhering state and the removal state based on being exposed to light having a wavelength in a range between 100-280 nm (e.g., in the UVC spectrum), light having a wavelength in a range between 280-315 nm (e.g., in the UVB spectrum), and/or light having a wavelength in a range between 315-400 nm (e.g., in the UVA spectrum). In some non-limiting embodiments, the light switchable adhesive is configured to transition between the adhering state and the removal state based on being exposed to light having a wavelength centered around 365 nm. In this way, the light switchable adhesive is configured to transition between the adhering state and the removal state based on being exposed to light having a wavelength provided by adhesive light source 106.

In some non-limiting embodiments, securement device 210 may include a transparent material. For example, securement device 210 may be made from (e.g., constructed of) a transparent material. In this way, light may be able to travel through securement device 210 and reach a light switchable adhesive and to cause the light switchable adhesive to transition from the adhering state to the removal state or to transition from the removal state to the adhering state. In some non-limiting embodiments, securement device 210 may include a transparent material that is transparent to light having a first wavelength (e.g., light having a specific wavelength, light having a specific wavelength in a range of wavelengths, etc.) and/or that is opaque to light having a second wavelength (e.g., which is different than the first wavelength).

In some non-limiting embodiments, support sections 114 contact the skin of a user, and allow for disinfecting light source 104, adhesive light source 106, and edge detection sensors 108 to be positioned a predetermined distance away from securement device 210 and the skin of the user. In some non-limiting embodiments, edge detection sensors 108 may be configured to be in contact (e.g., physical contact) with securement device 210 (e.g., a surface of securement device 210, such as a top surface of securement device 210). For example, edge detection sensors 108 may be positioned so that edge detection sensors 108 are in contact with securement device 210. In some non-limiting embodiments, disinfecting light source 104 and/or adhesive light source 106 may be configured to be in contact with securement device 210. For example, one or more light elements of disinfecting light source 104 and/or one or more light elements of adhesive light source 106 may be configured to be in contact with securement device 210. In some non-limiting embodiments, disinfecting light source 104 and/or adhesive light source 106 may be positioned away from securement device 210 and not in contact with securement device 210. For example, one or more light elements of disinfecting light source 104 and/or one or more light elements of adhesive light source 106 may be positioned away from securement device 210 and not in contact with securement device 210.

In some non-limiting embodiments, activation sensor 110 may detect contact with skin of the user by activation sensor 110 and/or whether the skin of the user is in proximity to activation sensor 110. In some non-limiting embodiments, activation sensor 110 may transmit a signal to a controller based on activation sensor 110 detecting contact with skin of the user by activation sensor 110 and/or that the skin of the user is in proximity to activation sensor 110. In some non-limiting embodiments, the controller may cause the one or more edge detection sensors 108 to detect the position of securement device 210 based on receiving the signal from activation sensor 110 that indicates that activation sensor 110 is in contact with the skin of the user and/or that the skin of the user is in proximity to activation sensor 110. In some non-limiting embodiments, edge detection sensors 108 may detect a position of securement device 210, which is covered by IV injection site processing device 100. For example, edge detection sensors 108 may detect a position of edges of securement device 210. In some non-limiting embodiments, edge detection sensors 108 may transmit a signal to the controller that indicates a position of the edges of securement device 210.

In some non-limiting embodiments, the controller may cause one or more light elements of disinfecting light source 104 and/or one or more light elements of adhesive light source 106 to activate that correspond to the position of securement device 210 based on the signal that indicates a position of the edges of securement device 210. Additionally or alternatively, the controller may forego causing one or more light elements of disinfecting light source 104 and/or one or more light elements of adhesive light source 106 to activate that do not correspond to the position of securement device 210.

Figure 3:
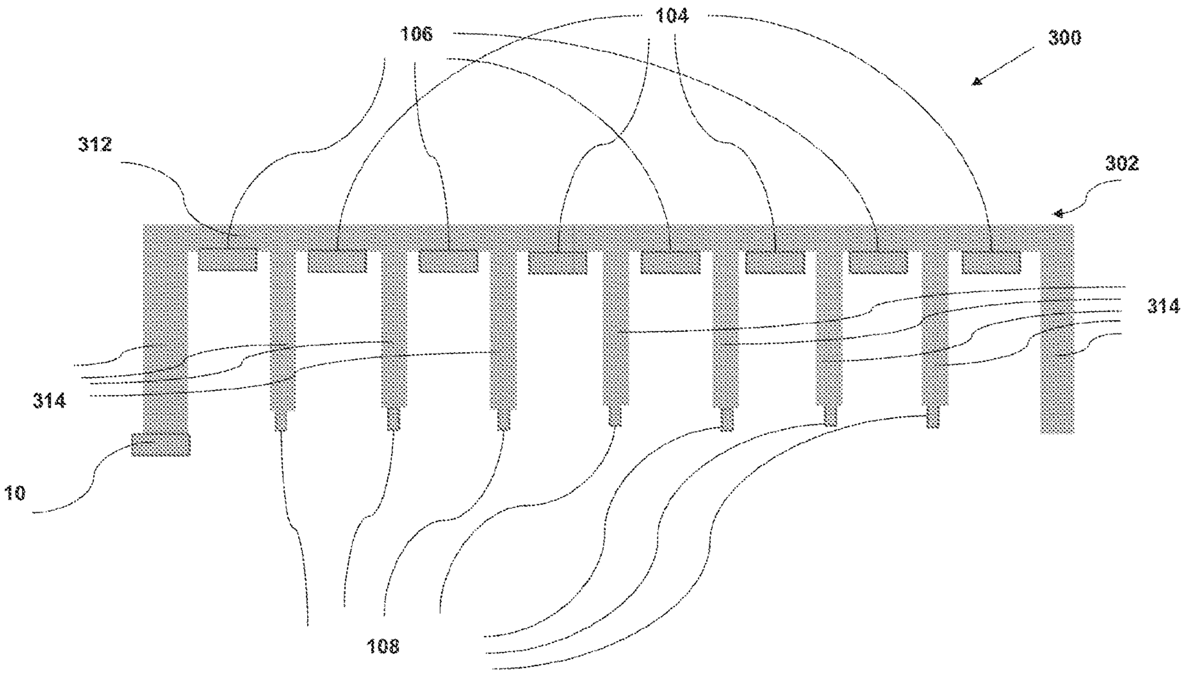
FIG. 3 is a diagram of a non-limiting embodiment of an IV injection site processing device.

Referring now to FIG. 3, FIG. 3 is a diagram of intravenous (IV) injection site processing device 300 and components thereof. As shown in FIG. 3, IV injection site processing device 300 may include housing 302, disinfecting light source 104, adhesive light source 106, edge detection sensors 108, and activation sensor 110. As shown in FIG. 3, housing 302 may include base section 312 and support sections 314 that are coupled to (e.g., formed on) base section 312 and extend away from base section 312. In some non-limiting embodiments, two or more support sections 314 (e.g., two support sections 314 positioned at edges of base section 312) are configured to contact an object, such as skin of a user, and allow for disinfecting light source 104, adhesive light source 106, edge detection sensors 108 to be positioned a distance away from the object.

In some non-limiting embodiments, housing 302 may be the same or similar to housing 102. For example, housing 302 may have a concave shape. In this way, IV injection site processing device 300 may be used to cover an IV injection site, such as an IV catheter insertion site, to provide a barrier to contamination of the IV injection site as well as providing light (e.g., in the form of electromagnetic radiation) that disinfects an object covered by IV injection site processing device 300 and/or is configured to cause a light switchable adhesive to transition between the adhering state and the removal state. In some non-limiting embodiments, base section 312 and/or support sections 314 of housing 302 may be the same or similar to base section 112 and/or support sections 114 of housing 102, respectively.

As shown in FIG. 3, a plurality of support sections 314 of housing 302 may be positioned between each light element of disinfecting light source 104 and adhesive light source 106. As further shown in FIG. 3, each of edge detection sensors 108 may be positioned on an end of the plurality of support sections 314 positioned between each light element and the other end of the plurality of support sections 314 may be coupled to (e.g., attached to) base section 312. In this way, the plurality of support sections 314 may allow for the light disinfecting light source 104 and adhesive light source 106 to be focused on locations of an object at an IV injection site that is covered by IV injection site processing device 300.

Although embodiments or aspects have been described in detail for the purpose of illustration and description, it is to be understood that such detail is solely for that purpose and that embodiments or aspects are not limited to the disclosed embodiments or aspects, but, on the contrary, are intended to cover modifications and equivalent arrangements that are within the spirit and scope of the appended claims. For example, it is to be understood that the present disclosure contemplates that, to the extent possible, one or more features of any embodiment or aspect can be combined with one or more features of any other embodiment or aspect. In fact, many of these features can be combined in ways not specifically recited in the claims and/or disclosed in the specification. Although each dependent claim listed below may directly depend on only one claim, the disclosure of possible implementations includes each dependent claim in combination with every other claim in the claim set.

What is claimed is:

1. A device comprising:

a housing comprising a base section, the housing configured to cover an object;

a disinfecting light source coupled to the base section of the housing and configured to provide light to one or more locations of the object, wherein the disinfecting light source is configured to disinfect the object covered by the housing;

an adhesive light source coupled to the base section of the housing and configured to provide light to the one or more locations of the object, wherein the adhesive light source is configured to cause a light switchable adhesive that is covered by the housing to transition between an adhering state and a removal state based on the light switchable adhesive being exposed to light emitted by the adhesive light source; and an activation sensor coupled to the housing, wherein the activation sensor is electrically coupled to the disinfecting light source and the adhesive light source, and wherein the activation sensor is configured to cause the disinfecting light source and the adhesive light source to activate.

2. The device of claim 1, wherein the disinfecting light source and the adhesive light source are configured to be activated based on a predetermined sequence.

3. The device of claim 1, wherein the disinfecting light source or the adhesive light source is configured to be deactivated based on an expiration of a time interval.

4. The device of claim 1, wherein the activation sensor is configured to:

detect a presence of a body of a user; and provide a signal to activate the disinfecting light source, the adhesive light source, or a combination of the disinfecting light source and the adhesive light source based on detecting the presence of the body of the user.

5. The device of claim 4, wherein the activation sensor is configured to:

provide a signal to deactivate the disinfecting light source, the adhesive light source, or a combination of the disinfecting light source and the adhesive light source based on failing to detect the presence of the body of the user.

6. The device of claim 1, wherein the adhesive light source provides light having a wavelength in a range of 315-400 nm.

7. The device of claim 1, wherein the disinfecting light source provides light having a wavelength in a range of 405-470 nm.

8. The device of claim 1, wherein the disinfecting light source or the adhesive light source comprises at least one light emitting diode (LED).

9. The device of claim 1, further comprising a plurality of edge detection sensors, wherein each edge detection sensor of the plurality of edge detection sensors is configured to detect an edge of an object.

10. The device of claim 9, wherein each edge detection sensor of the plurality of edge detection sensors is configured to provide an indication of a position of the object, and wherein the disinfecting light source and the adhesive light source are configured to be activated based on the position of the object.

11. The device of claim 9, wherein each edge detection sensor is configured to detect the edge of the object based on color, texture, conductivity, and/or any combination thereof.

12. The device of claim 1, wherein the housing comprises a base section and a plurality of support sections coupled to the base section, and wherein the base section and the plurality of support sections comprise a flexible material.

13. A device comprising:

a housing;

a disinfecting light source coupled to the housing, wherein the disinfecting light source is configured to disinfect an object covered by the housing;

an adhesive light source coupled to the housing, wherein the adhesive light source is configured to cause a light switchable adhesive to transition between an adhering state and a removal state based on the light switchable adhesive being exposed to light emitted by the adhesive light source; and an activation sensor coupled to the housing, wherein the activation sensor is electrically coupled to the disinfecting light source and the adhesive light source, and wherein the activation sensor is configured to cause the disinfecting light source and the adhesive light source to activate; and a plurality of edge detection sensors, wherein each edge detection sensor of the plurality of edge detection sensors is configured to detect an edge of an object;

wherein the activation sensor is configured to:

detect contact with a body of a user; and provide a signal to activate the disinfecting light source, the adhesive light source, or a combination of the disinfecting light source and the adhesive light source based on detecting contact with the body of the user; and wherein the disinfecting light source, the adhesive light source, or a combination of the disinfecting light source and the adhesive light source are configured to activate based on a signal received from one or more edge detection sensors and the signal provided by the activation sensor.

14. The device of claim 13, wherein each edge detection sensor of the plurality of edge detection sensors is configured to provide an indication of a position of the object, and wherein the disinfecting light source and the adhesive light source are configured to be activated based on the position of the object.

15. The device of claim 13, wherein the disinfecting light source comprises at least one light emitting diode (LED) that provides light having a wavelength in a range of 405-470 nm and wherein the adhesive light source provides light having a wavelength in a range of 315-400 nm.

16. An assembly comprising:

an intravenous (IV) injection site processing device comprising:

a housing comprising a base section, the housing configured to cover an object;

a disinfecting light source coupled to the base section of the housing and configured to provide light to one or more locations of the object, wherein the disinfecting light source is configured to disinfect an object;

an adhesive light source coupled to the base section of the housing and configured to provide light to the one or more locations of the object, wherein the adhesive light source is configured to cause a light switchable adhesive to transition between an adhering state and a removal state based on the light switchable adhesive being exposed to light emitted by the adhesive light source; and an activation sensor coupled to the housing, wherein the activation sensor is electrically coupled to the disinfecting light source and the adhesive light source, and wherein the activation sensor is configured to cause the disinfecting light source and the adhesive light source to activate; and a securement device, wherein the object comprises the securement device, and wherein the IV injection site processing device is configured to be positioned to cover the securement device.

17. The assembly of claim 16, wherein the disinfecting light source comprises at least one light emitting diode (LED) that provides light having a wavelength in a range of 405-470 nm and wherein the adhesive light source comprises at least one light emitting diode (LED) that provides light having a wavelength in a range of 315-400 nm.

18. The assembly of claim 16, wherein the securement device comprises the light switchable adhesive.

19. The assembly of claim 16, wherein the light switchable adhesive is configured to transition between the adhering state and the removal state based on the light switchable adhesive being exposed to light provided by the adhesive light source.

20. The assembly of claim 16, wherein the activation sensor is configured to:

detect contact with a body of a user; and provide a signal to activate the disinfecting light source, the adhesive light source, or a combination of the disinfecting light source and the adhesive light source based on detecting contact with the body of the user.

21. A device comprising:

a housing;

a disinfecting light source coupled to the housing, wherein the disinfecting light source is configured to disinfect an object covered by the housing; and an activation sensor coupled to the housing, wherein the activation sensor is electrically coupled to the disinfecting light source, and wherein the activation sensor is configured to cause the disinfecting light source to activate; and a plurality of edge detection sensors, wherein each edge detection sensor of the plurality of edge detection sensors is configured to detect an edge of the object; and wherein the activation sensor is configured to:

detect contact with a body of a user; and provide a signal to activate the disinfecting light source, based on detecting contact with the body of the user; and wherein the disinfecting light source is configured to activate based on a signal received from one or more edge detection sensors and the signal provided by the activation sensor.

22. The device of claim 21, wherein each edge detection sensor of the plurality of edge detection sensors is configured to provide an indication of a position of the object, and wherein the disinfecting light source is configured to be activated based on the position of the object.

23. The device of claim 21, wherein the disinfecting light source comprises at least one light emitting diode (LED) that provides light having a wavelength in a range of 405-470 nm.

24. A device comprising:

a housing;

an adhesive light source coupled to the housing, wherein the adhesive light source is configured to cause a light switchable adhesive covered by the housing to transition between an adhering state and a removal state based on the light switchable adhesive being exposed to light emitted by the adhesive light source; and an activation sensor coupled to the housing, wherein the activation sensor is electrically coupled to the adhesive light source, and wherein the activation sensor is configured to cause the adhesive light source to activate; and a plurality of edge detection sensors, wherein each edge detection sensor of the plurality of edge detection sensors is configured to detect an edge of an object; and wherein the activation sensor is configured to:

detect contact with a body of a user; and provide a signal to activate the adhesive light source based on detecting contact with the body of the user; and wherein the adhesive light source is configured to activate based on a signal received from one or more edge detection sensors and the signal provided by the activation sensor.

25. The device of claim 24, wherein each edge detection sensor of the plurality of edge detection sensors is configured to provide an indication of a position of the object, and wherein the adhesive light source is configured to be activated based on the position of the object.

26. The device of claim 24, wherein the adhesive light source provides light having a wavelength in a range of 315-400 nm.

* * * * *